(12) United States Patent
Bauduin

(10) Patent No.: US 9,585,798 B2
(45) Date of Patent: Mar. 7, 2017

(54) WATER ABSORBENT STORAGE LAYERS

(71) Applicant: BASF SE, Ludwigshafen (DE)

(72) Inventor: Christophe Bauduin, Plankstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/753,511

(22) Filed: Jun. 29, 2015

(65) Prior Publication Data
US 2015/0359688 A1 Dec. 17, 2015

Related U.S. Application Data

(63) Continuation of application No. 13/319,591, filed as application No. PCT/EP2010/056688 on May 17, 2010, now abandoned.

(30) Foreign Application Priority Data

May 20, 2009 (EP) .................................. 09160762

(51) Int. Cl.
| | | |
|---|---|---|
| A61F 13/15 | (2006.01) | |
| A61F 13/532 | (2006.01) | |
| A61F 13/53 | (2006.01) | |
| A61L 15/42 | (2006.01) | |
| A61L 15/60 | (2006.01) | |
| A61F 13/511 | (2006.01) | |

(Continued)

(52) U.S. Cl.
CPC ........ *A61F 13/5323* (2013.01); *A61F 13/511* (2013.01); *A61F 13/51401* (2013.01); *A61F 13/53* (2013.01); *A61F 13/539* (2013.01); *A61L 15/22* (2013.01); *A61L 15/24* (2013.01); *A61L 15/26* (2013.01); *A61L 15/28* (2013.01); *A61L 15/42* (2013.01); *A61L 15/425* (2013.01); *A61L 15/58* (2013.01); *A61L 15/60* (2013.01); *A61F 13/531* (2013.01); *A61F 2013/530007* (2013.01); *A61F 2013/530131* (2013.01); *A61F 2013/530481* (2013.01); *A61F 2013/530802* (2013.01); *A61F 2013/53941* (2013.01); *Y10T 442/699* (2015.04)

(58) Field of Classification Search
CPC ....... A61F 13/539; A61F 13/531; A61F 13/53
USPC .................................. 604/367, 370, 368, 378
See application file for complete search history.

(56) References Cited

U.S. PATENT DOCUMENTS

| | | |
|---|---|---|
| 4,994,053 A | 2/1991 | Lang |
| 5,030,314 A | 7/1991 | Lang |

(Continued)

FOREIGN PATENT DOCUMENTS

| | | |
|---|---|---|
| EP | 0 374 910 A1 | 6/1990 |
| EP | 0 765 649 A2 | 4/1997 |

(Continued)

OTHER PUBLICATIONS

Buchholz, F.L., et al., "Applications of Superabsorbent Polymers," *Modern Superabsorbent Polymer Technology*, New York: John Wiley & Sons, Inc., 1998, pp. 252-258.

(Continued)

*Primary Examiner* — Jacqueline Stephens
(74) *Attorney, Agent, or Firm* — Marshall, Gerstein & Borun LLP

(57) ABSTRACT

The present invention relates to improved water-absorbing storage layers for use in hygiene articles, the water-absorbing storage layers being essentially free of cellulose fibers.

10 Claims, 2 Drawing Sheets

(51) Int. Cl.
*A61F 13/514* (2006.01)
*A61F 13/539* (2006.01)
*A61L 15/22* (2006.01)
*A61L 15/24* (2006.01)
*A61L 15/26* (2006.01)
*A61L 15/28* (2006.01)
*A61L 15/58* (2006.01)
*A61F 13/531* (2006.01)

(56) References Cited

U.S. PATENT DOCUMENTS

| | | | |
|---|---|---|---|
| 5,494,622 A | 2/1996 | Heath et al. | |
| 5,700,254 A | 12/1997 | McDowall et al. | |
| 6,136,873 A | 10/2000 | Hahnle et al. | |
| 6,414,214 B1 | 7/2002 | Engelhardt et al. | |
| 8,013,087 B2 | 9/2011 | Losch et al. | |
| 2003/0135172 A1 | 7/2003 | Whitmore et al. | |
| 2003/0181115 A1 | 9/2003 | Nagasuna et al. | |
| 2004/0167486 A1 | 8/2004 | Busam et al. | |
| 2005/0137085 A1 | 6/2005 | Zhang et al. | |
| 2006/0004336 A1 | 1/2006 | Zhang et al. | |
| 2007/0066754 A1* | 3/2007 | Loeker | A61L 15/60 525/127 |
| 2007/0135785 A1 | 6/2007 | Qin et al. | |
| 2007/0156108 A1 | 7/2007 | Becker et al. | |
| 2008/0125735 A1 | 5/2008 | Busam et al. | |
| 2008/0161522 A1 | 7/2008 | Riegel et al. | |
| 2008/0312617 A1* | 12/2008 | Hundorf | A61F 13/15658 604/366 |
| 2008/0312623 A1 | 12/2008 | Hundorf et al. | |
| 2012/0064792 A1 | 3/2012 | Bauduin | |

FOREIGN PATENT DOCUMENTS

| | | |
|---|---|---|
| EP | 1 088 537 A2 | 4/2001 |
| EP | 1 447 066 A1 | 8/2004 |
| EP | 1 447 067 A1 | 8/2004 |
| EP | 1 504 772 A1 | 2/2005 |
| EP | 1 808 152 A2 | 7/2007 |
| EP | 1 813 236 A2 | 8/2007 |
| EP | 1 813 237 A2 | 8/2007 |
| EP | 1 911 425 A2 | 4/2008 |
| EP | 1 911 426 A2 | 4/2008 |
| EP | 1 913 912 A1 | 4/2008 |
| EP | 1 913 913 A2 | 4/2008 |
| EP | 1 913 914 A2 | 4/2008 |
| EP | 1 917 940 A2 | 5/2008 |
| JP | S54130686 A | 10/1979 |
| JP | H0226555 A | 1/1990 |
| JP | 2001178774 A | 7/2001 |
| WO | WO-95/11651 A1 | 5/1995 |
| WO | WO-95/11652 A1 | 5/1995 |
| WO | WO-95/11653 A1 | 5/1995 |
| WO | WO-95/11654 A1 | 5/1995 |
| WO | WO-95/21596 A1 | 8/1995 |
| WO | WO-97/05841 A1 | 2/1997 |
| WO | WO-97/17397 A1 | 5/1997 |
| WO | WO-01/15646 A1 | 3/2001 |
| WO | WO-01/25290 A1 | 4/2001 |
| WO | WO-02/094328 A2 | 11/2002 |
| WO | WO-2008/040715 A2 | 4/2008 |
| WO | WO-2008/155699 A1 | 12/2008 |
| WO | WO-2008/155701 A2 | 12/2008 |
| WO | WO-2008/155702 A1 | 12/2008 |
| WO | WO-2008/155710 A1 | 12/2008 |
| WO | WO-2008/155711 A1 | 12/2008 |
| WO | WO-2008/155722 A2 | 12/2008 |
| WO | WO-2009/022277 A1 | 2/2009 |
| WO | WO-2010/015560 A1 | 2/2010 |
| WO | WO-2010/015561 A1 | 2/2010 |
| WO | WO-2010/015591 A1 | 2/2010 |
| WO | WO-2010/133529 A2 | 11/2010 |
| WO | WO-2012/048879 A1 | 4/2012 |

OTHER PUBLICATIONS

International Search Report in international application No. PCT/EP2010/056688, dated Jan. 18, 2011 (English translation).

* cited by examiner

WATER ABSORBENT STORAGE LAYERS

The present invention relates to improved water-absorbing storage layers for use in hygiene articles, the water-absorbing storage layers being essentially free of cellulose fibers.

The production of water-absorbing polymer particles and the use thereof for producing hygiene articles is described, for example, in the monograph "Modern Superabsorbent Polymer Technology", F. L. Buchholz and A. T. Graham, Wiley-VCH, 1998, especially on pages 252 to 258. The water-absorbing polymer particles are also referred to as superabsorbents.

The currently commercially available disposable diapers consist typically of a liquid-pervious topsheet (A), a liquid-impervious backsheet (B), a water-absorbing storage layer (C) between layers (A) and (B), and an acquisition distribution layer (D) between layers (A) and (C).

The water-absorbing storage layer consists typically of a mixture of water-absorbing polymer particles and cellulose fibers, the water-absorbing polymer particles being fixed by the cellulose matrix.

In the last few years, there has been a trend toward ever thinner disposable diapers. To produce ever thinner disposable diapers, the proportion of cellulose fibers in the water-absorbing storage layer has been lowered ever further. A disadvantage here is that the cellulose matrix is made ever thinner as a result, and the mobility of the water-absorbing polymer particles in the water-absorbing storage layer increases.

Especially when water-absorbing storage layers essentially free of cellulose fibers are desired, i.e. consist virtually exclusively of water-absorbing polymer particles, there is the risk that the water-absorbing polymer particles will slip within the disposable diaper or even fall out of the disposable diaper completely.

To solve this problem, novel water-absorbing storage layers have been produced. For example, WO 97/17397 A1 describes a process for producing water-absorbing foams.

Use of such foams allows the use of cellulose fibers to be dispensed with entirely.

Cellulose-free hygiene articles can also be secured to suitable nonwoven backsheets by fixing of water-absorbing polymer particles by means of thermoplastic polymers, especially of hotmelt adhesives, provided that these thermoplastic polymers are spun out to form fine fibers. Such products are described, for example, in US 2003/0181115, US 2004/0167486, US 2004/071363, US 2005/097025, US 2007/156108, US 2008/0125735, EP 1 917 940 A1, EP 1 913 912 A1, EP 1 913 913 A2, EP 1 913 914 A2, EP 1 911 425 A2, EP 1 911 426 A2, EP 1 447 067 A1, EP 1 813 237 A2, EP 1 813 236 A2, EP 1 808 152 A2, EP 1 447 066 A1. The production processes are disclosed in WO 2008/155722 A2, WO 2008/155702 A1, WO 2008/155711 A1, WO 2008/155710 A1, WO 2008/155701 A2, WO 2008/155699 A1. A disadvantage is the relatively complex production process, since the spinning of the adhesive fibers in the presence of water-absorbing polymer particles is difficult and prone to faults.

In addition, extensible cellulose-free hygiene articles are known, and US 2006/0004336, US 2007/0135785, and US 2005/0137085 disclose production thereof by simultaneous fiber spinning of suitable thermoplastic polymers and incorporation of water-absorbing polymer particles. This process too is complex and prone to faults.

It was an object of the present invention to provide improved water-absorbing storage layers for hygiene articles, especially disposable diapers. For the improved water-absorbing storage layers, it should be possible to use the customary water-absorbing polymer particles. Moreover, the improved water-absorbing storage layers should be essentially free of cellulose fibers, and the water-absorbing polymer particles in the water-absorbing storage layer should neither slip nor fall out either in the dry or moist state. In the context of this application, "free of cellulose fibers" means that the cellulose content in the inventive storage layer is preferably less than 30% by weight, preferentially less than 20% by weight, more preferably less than 10% by weight, most preferably less than 5% by weight. Ideally, no cellulose at all is present.

The object is achieved by water-absorbing storage layers consisting of a nonwoven backsheet, water-absorbing polymer particles and a liquid-pervious topsheet, wherein the water-absorbing polymer particles are fixed on the nonwoven backsheet.

In one embodiment of the present invention, the liquid-pervious topsheet is adhesive bonded to the nonwoven backsheet to form pockets. For this purpose, customary adhesives can be used. However, it is also possible that the liquid-pervious topsheet and/or nonwoven backsheet is entirely or partly composed of a thermoplastic polymer, and the liquid-pervious topsheet is adhesive bonded to the nonwoven backsheet by partial melting. Suitable nonwoven backsheets may consist of mixtures of thermoplastic fibers (for example polyolefins, polyesters, polyamides) and non-thermoplastic fibers (for example cellulose).

The formation of pockets filled with water-absorbing polymer particles imparts the form of a quilt to the water-absorbing storage layer. The water-absorbing polymer particles are prevented from slipping within the water-absorbing storage layer by the pockets.

In a further preferred variant of this embodiment, the depressions are partly filled with a liquid-conducting filler material and the pockets are optionally also additionally covered thereby. Useful filler materials for this purpose include hydrophilic fibers alone (for example cellulose, viscose or rayon) or in a mixture with other fibers (for example propylene or cellulose acetate). The fibers may also be those which consist of more than one component and which have a bi- or multilamellar or hollow cross section. Such fibers typically conduct the liquid better than simple smooth fibers.

Advantageously, the depressions formed in the water-absorbing storage layer by virtue of the adhesive bonding of the liquid-pervious topsheet to the nonwoven backsheet are filled with further water-absorbing polymer particles and fixed to a further liquid-pervious topsheet.

Figure 1A:
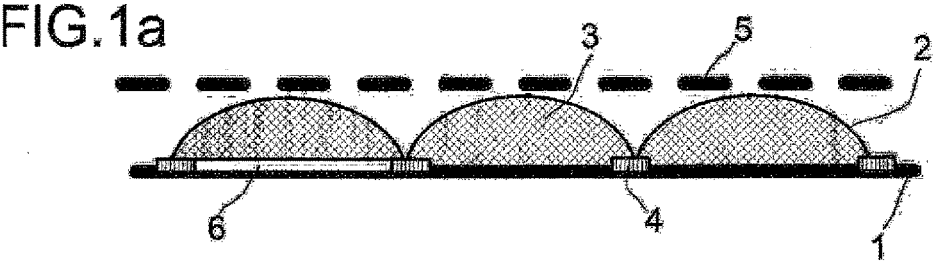
FIG. 1A and FIG. 1B are cross-sections of embodiments of the inventive water-absorbing storage layers.
Figure 1B:
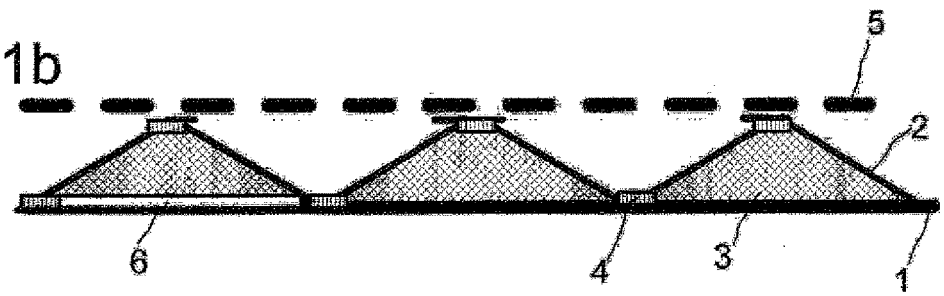
Figure 1C:
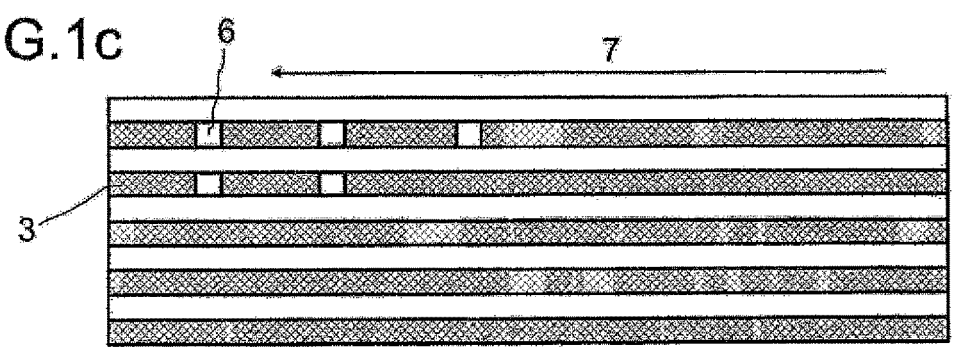
FIG. 1C is a longitudinal view of the embodiments of FIG. 1A and FIG. 1B.

FIGS. 1*a* and 1*b* show cross sections, and FIG. 1*c* shows a longitudinal section, of the inventive water-absorbing storage layers of the first embodiment, the reference numerals having the following meanings:

1 nonwoven backsheet
2 liquid-pervious topsheet
3 water-absorbing polymer particles
4 adhesive bond
5 second liquid-pervious topsheet
6 additional adhesive bond
7 machine running direction.

In a second embodiment of the present invention, a nonwoven substrate with preferably hydrophilic fibers protruding upward is used. The water-absorbing polymer particles are fixed by the fibers between the nonwoven backsheet and the liquid-pervious topsheet. The liquid-pervious topsheet is preferably adhesive bonded to the fibers of the nonwoven backsheet. The fibers protruding upward may consist of all known polymers and mixtures thereof, but preference is given to polyolefins, polyesters, polyurethanes, cellulose and derivatives thereof, polyamides. The fibers may also be those which consist of more than one component and which have a bi- or multilamellar or hollow cross section.

Figure 2:
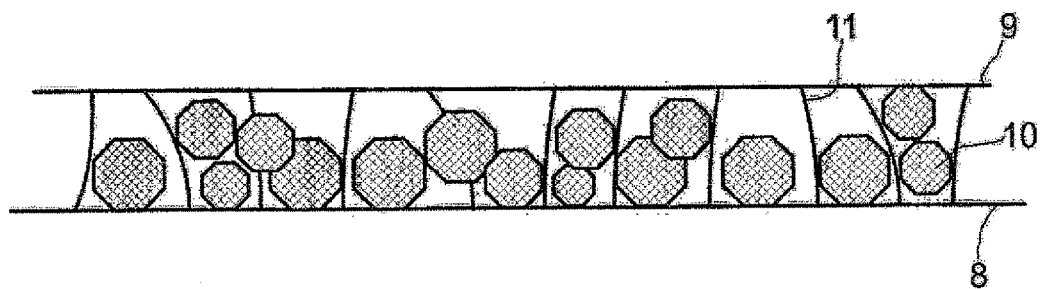
FIG. 2 is a cross-section of an inventive water-absorbing layer showing an embodiment containing fibers.

FIG. 2 shows a cross section of the inventive water-absorbing storage layers of the second embodiment, the reference numerals having the following meanings:

8 nonwoven backsheet
9 liquid-pervious topsheet
10 water-absorbing polymer particles
11 fibers directed upward.

In a third embodiment of the present invention, a soft matrix composed of a liquid-pervious material is applied to the nonwoven backsheet, and the water-absorbing polymer particles are introduced into the chambers of the matrix. The chambers of the matrix are sealed with a liquid-pervious topsheet. The soft matrix is preferably adhesive bonded to the nonwoven backsheet and the liquid-pervious topsheet.

An advantage of this embodiment is that the matrix material can be selected such that it additionally promotes liquid distribution within the water-absorbing storage layer. Suitable for this purpose are pressed hydrophilic fibers (for example of cellulose, chemically precipitated cellulose or crosslinked cellulose), or open-pore soft sponges. In the case of sponges, hydrophilic types are preferred. The matrix material should have, in the expanded state (unpressed), continuous pores with diameter preferably of 0.001 to 2.0 mm, preferably of 0.01 to 1.0 mm, more preferably of 0.03 to 0.5 mm, most preferably of 0.06 to 0.3 mm.

Figure 3A:
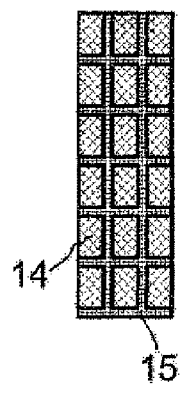
FIG. 3A is a top-view of an embodiment of the inventive water-absorbing storage layer having a liquid-pervious matrix.
Figure 3B:
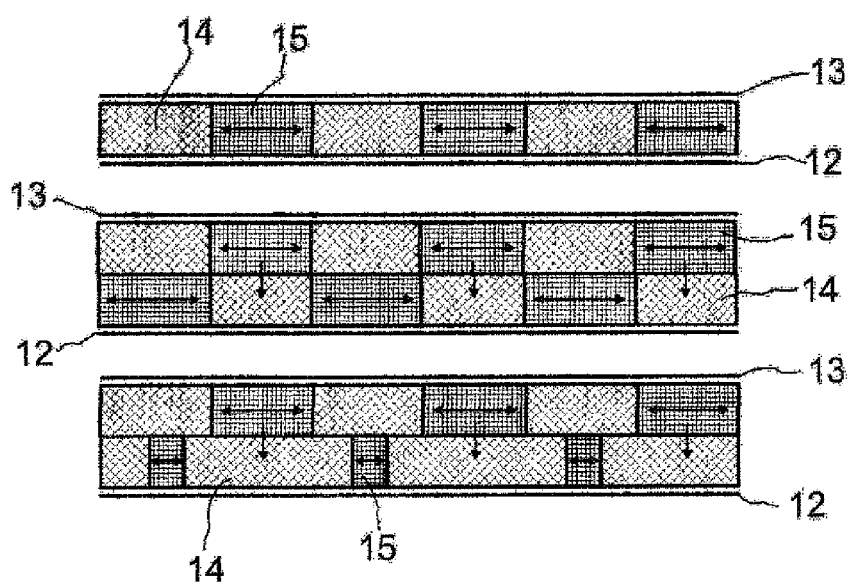
FIG. 3B contains cross sections of inventive water-absorbing storage layer having a liquid pervious matrix.

FIG. 3a shows a top view, and FIG. 3b shows cross sections, of the inventive water-absorbing storage layers of the third embodiment, the reference numerals having the following meanings:

12 nonwoven backsheet
13 liquid-pervious topsheet
14 water-absorbing polymer particles
15 liquid-pervious matrix.

In all embodiments, in a further particularly preferred variant, it is additionally possible to use a water-soluble adhesive for dry fixing of the water-absorbing polymer particles. The adhesive is applied, for example, to the nonwoven backsheet before the application of the water-absorbing polymer particles. The application can be effected, for example, in punctiform fashion, over the whole area, or preferably in strips in or transverse to or diagonally with respect to the machine running direction. The water-soluble adhesive may consist, for example, of polyvinyl alcohol, polyvinylpyrrolidone, polyethylene glycol, starch and starch derivatives, cellulose and cellulose derivatives, or polyacrylic acid. Most preferably, the water-soluble adhesive comprises at least one polyamine or consists thereof. Suitable polyamines are polyvinylamines, polyethyleneimines, polyallylamines. Particular preference is given to polyvinylamine. On contact with moisture, the amine is released from the adhesive and becomes attached to the swelling hydrogel, which additionally causes a particular gel layer stability in the swollen state.

In preferred embodiments, a web of the nonwoven backsheet is moved in machine direction, and strips or geometric patterns comprising water-absorbing polymer particles are applied thereto. In the second embodiment of the present invention, a continuous surface may be obtained in this way. In all three embodiments, however, any desired geometric forms and patterns are conceivable, for example one which are arranged like cushions comprising water-absorbing polymer particles in terms of area. The cushions or the heaps of water-absorbing polymer particles applied may assume any desired shape in terms of area, for example circles, ellipses, rectangles, squares, triangles (viewed from above). Particular preference is given to any desired polygons or mixtures of polygons with which the two-dimensional surface can be covered without gaps. Particular preference is also given to the application of one or more continuous strips in machine running direction, the strips running parallel to one another.

In the case of pockets, it is advantageous to fill them loosely, in order that the water-absorbing polymer particles can swell in a substantially unhindered manner. Optionally, however, an elastic nonwoven can also be used as a topsheet or as a backsheet. Such nonwovens are commercially available.

In all embodiments, the nonwoven backsheet is fixed on a suitable machine by means of reduced pressure such that water-absorbing polymer particles to be laid on can then be laid on there by means of masks or similar means, such that these water-absorbing polymer particles are held fixed from below by the existing suction during processing. It is thus equally possible to temporarily fix the other components.

A. Water-Absorbing Polymer Particles

The water-absorbing polymer particles are produced by polymerizing a monomer solution or suspension and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water. Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight, most preferably 0.3 to 0.6% by weight, based in each case on monomer a). With rising crosslinker content, the centrifuge retention capacity (CRC) falls and the absorption under a pressure of 21.0 $g/cm^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Bruggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight, most preferably 2 to 8% by weight, the residual moisture content being determined by EDANA (European Disposables and Nonwovens Association) recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained (fines). The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm, very particularly from 300 to 500 μm. The mean particle size of the product fraction may be determined by means of EDANA (European Disposables and Nonwovens Association) recommended test method No. WSP 220.2-05 "Particle Size Distribution", where the proportions by mass of the screen fractions are plotted in cumulated form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the saline flow conductivity or gel bed permeability (SFC or GBP). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until in an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

The proportion of particles having a particle size of at most 600 μm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617

A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate, tartate, citrate and lactate. Aluminum sulfate, basic aluminum acetate and aluminum lactate are preferred. Apart from metal salts, it is also possible to use polyamines as polyvalent cations.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio is preferably from 20:80 to 40:60.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range from 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

Subsequently, the surface postcrosslinked polymer particles can be classified again, excessively small and/or excessively large polymer particles being removed and recycled into the process.

To further improve the properties, the surface postcrosslinked polymer particles can be coated or remoisturized.

The optional remoisturizing is carried out preferably at 30 to 80° C., more preferably at 35 to 70° C. and most preferably at 40 to 60° C. At excessively low temperatures, the water-absorbing polymer particles tend to form lumps, and, at higher temperatures, water already evaporates noticeably. The amount of water used for remoisturizing is preferably from 1 to 10% by weight, more preferably from 2 to 8% by weight and most preferably from 3 to 5% by weight. The remoisturizing increases the mechanical stability of the polymer particles and reduces their tendency to static charging.

Suitable coatings for improving the swell rate and the saline flow conductivity or gel bed permeability (SFC or GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20.

The water-absorbing polymer particles produced by the process according to the invention have a moisture content of preferably 0 to 15% by weight, more preferably 0.2 to 10% by weight, most preferably 0.5 to 8% by weight, the moisture content being determined by EDANA (European Disposables and Nonwovens Association) recommended test method No. WSP 230.2-05 "Moisture Content".

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by EDANA (European Disposables and Nonwovens Association) recommended test method No. WSP 241.2-05 "Centrifuge Retention Capacity".

The water-absorbing polymer particles produced by the process according to the invention have an absorption under a pressure of 49.2 g/cm$^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to EDANA (European Disposables and Nonwovens Association) recommended test method No. WSP 242.2-05 "Absorption under Pressure", except that a pressure of 49.2 g/cm$^2$ is established instead of a pressure of 21.0 g/cm$^2$.

B. Hygiene Articles

The hygiene articles, especially disposable diapers, consist of
  (A) an upper liquid-pervious layer,
  (B) a lower liquid-impervious layer,
  (C) a water-absorbing storage layer (core) between layer (A) and layer (B), and
  (D) optionally an acquisition distribution layer between layer (A) and layer (C).

The upper liquid-pervious layer (A) is the layer which has direct contact with the skin. The material for this consists of customary synthetic or semisynthetic fibers, such as polyesters, polyolefins and rayon, or of customary natural fibers, such as cotton. In the case of nonwoven materials, the fibers should generally be bonded by binders such as polyacrylates. Preferred materials are polyester, rayon, polyethylene and polypropylene. Examples of liquid-pervious layers are described, for example, in WO 99/57355 A1 and EP 1 023 883 A2.

The lower liquid-impervious layer (B) consists typically of a polyethylene or polypropylene film. However, it may also consist of any other film-forming polymer, for example of polyester, polyamide, especially biodegradable polyester.

The inventive water-absorbing storage layers are essentially free of cellulose fibers or have a proportion of cellulose fibers of preferably less than 30% by weight, preferentially less than 20% by weight, more preferably less than 10% by weight, most preferably less than 5% by weight. The water-absorbing polymer particles usable are not subject to any restriction. Preference is given, however, to using water-absorbing polymer particles with a saline flow conductivity (SFC) of 50 to 150×10$^{-7}$ cm$^3$ s/g, the saline flow conductivity (SFC) being determinable by the method described in WO 2008/092843 A1 (page 30, lines 16 to 36).

It is likewise possible to use water-absorbing polymer particles with a gel bed permeability (GBP) of 10 to 100 darcies. In a particular embodiment, water-absorbing polymer particles with a gel bed permeability (GBP) of 100 to 1000 darcies are used. The gel bed permeability (GBP) is determined to US 2005/0256757.

It is additionally advantageous to use water-absorbing polymer particles with a centrifuged retention capacity (CRC) of at least 33 g/g and an absorption under pressure of 49.2 g/cm$^2$ (AUL0.7 psi) of at least 12 g/g.

It is additionally advantageous when the absorption rate of the water-absorbing polymer particles for aqueous body fluids is adjusted optimally to the particular demands in the water-absorbing storage layer. To determine the absorption rate, preference is given to using the vortex test described in the literature, for example in the monograph "Modern Superabsorbent Polymer Technology". F. L. Buchholz and A. T. Graham, Wiley-VCH, 1998, on pages 156 and 157. The vortex times of the water-absorbing polymer particles should be less than 120 seconds, preferably less than 80 seconds, preferentially less than 50 seconds, more preferably less than 40 seconds, most preferably less than 20 seconds.

The acquisition distribution layer (D) consists typically of cellulose fibers, modified cellulose or synthetic fibers, and has the task of rapidly absorbing aqueous liquids, for example urine, and passing them on to the water-absorbing layer (C).

For the acquisition distribution layer (D), preferably modified, more preferably chemically modified, most preferably chemically stiffened, cellulose fibers are used. Suitable agents for chemical stiffening are cationically modified starches, polyamide-epichlorohydrin resins, polyacrylamides, urea-formaldehyde resins, melamine-formaldehyde resins and polyethyleneimine resins.

The stiffening can also be effected by modifying the chemical structure, for example by crosslinking. The crosslinkers can crosslink the polymer chains by formation of covalent bonds. Suitable crosslinkers are, for example, $C_2$- to $C_8$-dialdehydes, $C_2$- to $C_8$-monoaldehydes with a carboxylic acid group and $C_2$- to $C_8$-dicarboxylic acids.

According to the present invention, improved water-absorbing storage layers are obtained, as are hygiene articles which comprise them. The separation of liquid storage and liquid conduction can firstly significantly lower material consumption, especially of fibers, for production of the storage layers; secondly, thin and soft hygiene articles are obtained, which have outstanding integrity when dry and in use, since the water-absorbing polymer particles can be fixed significantly more efficiently.

The invention claimed is:

1. A water-absorbing storage layer consisting of a nonwoven backsheet, water-absorbing polymer particles, a liquid-pervious matrix, an adhesive, and a liquid-pervious topsheet, wherein liquid-pervious matrix is arranged in strips or geometric patterns between the liquid-pervious topsheet and the nonwoven backsheet and the water-absorbing polymer particles are present in chambers formed by the liquid-pervious matrix, wherein the water-absorbing polymer particles are fixed on the nonwoven backsheet; and
  wherein the liquid-pervious matrix is selected from the group consisting of a hydrophilic fiber, cellulose, and a sponge.

2. The storage layer according to claim 1, wherein the water-absorbing polymer particles have a centrifuge retention capacity of at least 15 g/g.

3. A hygiene article comprising a water-absorbing storage layer according to claim 1.

4. The storage layer of claim 1 wherein the liquid-pervious matrix is adhesively bonded to the nonwoven backsheet and the liquid-pervious topsheet.

5. The storage layer of claim 1 wherein the liquid-pervious matrix has continuous pores having a diameter of 0.001 to 2.0 mm.

6. The storage layer according to claim 1, wherein the nonwoven backsheet has fibers directed upward and the water-absorbing polymer particles are present in the region of the fibers.

7. The storage layer according to claim 1, further consisting of a second adhesive, wherein the second adhesive fixes the water-absorbing polymer particles to the nonwoven backsheet.

8. The storage layer according to claim 7, wherein the second adhesive is a water-soluble adhesive.

9. The storage layer according to claim 8, wherein the water-soluble adhesive is selected from the group consisting of polyvinyl alcohol, polyvinylpyrrolidone, polyethylene glycol, starch and starch derivatives, cellulose and cellulose derivatives, polyacrylic acid, polyvinylamine, polyethyleneimine, and polyallylamine.

10. The storage layer according to claim 1 wherein the liquid-pervious topsheet is selected from the group consisting of a polyester, a polyolefin, rayon, and cotton.

* * * * *